US008568778B2

(12) United States Patent
Lizio et al.

(10) Patent No.: US 8,568,778 B2
(45) Date of Patent: Oct. 29, 2013

(54) MULTIPARTICULATE FORM OF ADMINISTRATION, COMPRISING NUCLEIC ACID-CONTAINING MUCOADHESIVE ACTIVE INGREDIENTS, AND METHOD FOR PRODUCING SAID FORM OF ADMINISTRATION

(75) Inventors: Rosario Lizio, Rossdorf (DE);
 Hans-Ulrich Petereit, Darmstadt (DE);
 Dave Trupti, Zwingenberg (DE);
 Michael Gottschalk, Ober-Ramstadt (DE)

(73) Assignee: Evonik Röhm GmbH, Darmstadt (DE)

( * ) Notice: Subject to any disclaimer, the term of this patent is extended or adjusted under 35 U.S.C. 154(b) by 1117 days.

(21) Appl. No.: 11/721,399

(22) PCT Filed: Nov. 5, 2005

(86) PCT No.: PCT/EP2005/011864
§ 371 (c)(1),
(2), (4) Date: Jun. 11, 2007

(87) PCT Pub. No.: WO2006/061069
PCT Pub. Date: Jun. 15, 2006

(65) Prior Publication Data
US 2009/0280183 A1 Nov. 12, 2009

(30) Foreign Application Priority Data
Dec. 10, 2004 (DE) .......................... 10 2004 059 792

(51) Int. Cl.
*A61K 9/20* (2006.01)
(52) U.S. Cl.
USPC ........ 424/487; 424/130.1; 424/488; 424/484; 977/906; 514/44 R
(58) Field of Classification Search
None
See application file for complete search history.

(56) References Cited

U.S. PATENT DOCUMENTS

| 6,465,626 | B1 | 10/2002 | Watts et al. |
| 2003/0166783 | A1 | 9/2003 | Davis et al. |
| 2004/0224019 | A1* | 11/2004 | Shefer et al. ................. 424/469 |
| 2006/0269605 | A1 | 11/2006 | Lizio et al. |
| 2007/0026082 | A1 | 2/2007 | Lizio et al. |
| 2007/0042045 | A1 | 2/2007 | Lizio et al. |
| 2008/0026051 | A1 | 1/2008 | Lizio et al. |
| 2008/0166416 | A1 | 7/2008 | Lizio et al. |

FOREIGN PATENT DOCUMENTS

| CA | 2 532 487 | A1 | 1/2005 |
| EP | 0 514 008 | | 11/1992 |
| EP | 1 203 590 | | 5/2002 |
| JP | 2001-508641 | | 7/2001 |
| WO | WO 2004/052339 | A1 | 6/2004 |

OTHER PUBLICATIONS

Roy et al "Oral gene delivery with chitosan-DNA nanoparticles generates immunologic protection in a murine model of peanut allergy," Nature Medicine, 5)4): 387-391 (Apr. 1999).*
Roy et al "Oral gene delivery with chitosan-DNA nanoparticles generates immunologic protection in a murine model of peanut allergy," Nature Medicine, 5(4): 387-391 (Apr. 1999).*
U.S. Appl. No. 11/815,632, filed Aug. 6, 2007, Lizio, et al.
Hejazi Radi, et al., "Chitosan-Based Gastrointestinal Delivery Systems", Journal of Controlled Release, vol. 89, No. 2, XP 004421352, p. 151-165, 2003.
Roy Krishnendu, et al., "Oral Gene Delivery With Chitosan-DNA Nanoparticles Generates Immunologic Protection in a Murine Model of Peanut Allergy", Nature Medicine, vol. 5, No. 4, XP 002148464, p. 387-391, 1999.
Office Action issued Apr. 11, 2011, in Canada Patent Application No. 2,586,597.
Search Report issued Mar. 25, 2011, in Japan Patent Application No. 2007-544750.
M. L. Lorenzo-Lamosa, et al., "Design of microencapsulated chitosan microspheres for colonic drug delivery", Journal of Controlled Release 52, Elsevier, 1998, pp. 109-118.
K. A. Janes, et al., "Polysaccharide colloidal particles as delivery systems for macromolecules", Advanced Drug Delivery Reviews 47, Elsevier, 2001, pp. 83-97.
Igaku no ayumi (Weg der Medizin), veroffentlicht: Aug. 2004, vol. 210 No. 9, pp. 726-729 (Design of drug delivery system with nanotechnology) with partial English translation.
Office Action issued Apr. 3, 2012, in Canadian Patent Application No. 2,586,597.

* cited by examiner

*Primary Examiner* — Suzanne Ziska
(74) *Attorney, Agent, or Firm* — Oblon, Spivak, McClelland, Maier & Neustadt, L.L.P.

(57) ABSTRACT

The invention relates to an oral, multiparticulate form of administration, comprising pellets in the size ranging from 50 to 2500 $g(m)m which are substantially constituted of a) an inner matrix layer containing nanoparticles that contain a nucleic acid active ingredient and being embedded in a matrix of a polymer having a mucoadhesive effect, and b) an outer film coating, substantially consisting of an anionic polymer or copolymer that is optionally formulated with pharmaceutically conventional adjuvants, especially emollients.

26 Claims, No Drawings

MULTIPARTICULATE FORM OF ADMINISTRATION, COMPRISING NUCLEIC ACID-CONTAINING MUCOADHESIVE ACTIVE INGREDIENTS, AND METHOD FOR PRODUCING SAID FORM OF ADMINISTRATION

The invention relates to a multiparticulate pharmaceutical form comprising mucoadhesively formulated nucleic acid active ingredients, and to a process for producing the pharmaceutical form.

PRIOR ART

WO 02/64148 describes formulations comprising a mucopolysaccharide and a process for producing them. In this case, a mucopolysaccharide, e.g. heparin, is formulated together with an adsorption enhancer, e.g. a chitosan, and subsequently provided with a coating soluble in intestinal juice, so that the active ingredient can be released in the middle or lower segments of the small intestine. Examples of suitable coatings soluble in intestinal juice are anionic acrylic copolymers of the type of Eudragit® L, S, L100-55. The formulations may include capsules, tablets and granules.

Telomerase is an enzyme which, in cell divisions, contributes for DNA doubling, especially in the region of the chromosome ends. The enzyme is therefore important for maintaining an intact chromosome structure. Telomerase activity is repressed in most adult body cells, an elevated telomerase activity being observed not only in germ cells, but also in many tumour cell types. It is presumed that telomerase plays an important role in the molecular control of the normal life cycle of cells until their genetically preprogrammed cell death. The high telomerase activity, differing from normal cells, in tumour cells is interpreted as a sign chat normal cell division control has gone astray. Telomerase and the gene structures associated therewith are regarded as a starting point for the genetic therapy of tumour cells.

WO 99/38964 describes nucleic acids for gene therapy which comprise in particular a telomerase gene promoter. This DNA can be coupled to heterologous genes such as, for example, cytotoxin-encoding genes. The nucleic acid construct can be employed as active ingredient for transfection of tumour cells with elevated telomerase activity. The expectation is that this will inhibit tumour cell division and even specifically kill these cells. The possibility of oral administration, of the active ingredient types described in WO 99/38964, and of pharmaceutical forms derived therefrom, is mentioned.

Roy et al. (1999) describes in *Nature Medicine, Vol. 5, No. 4*, pp. 387-391, *"Oral gene delivery with chitosan-DNA nanoparticles generates immunologic protection in murine model of peanut allergy"* oral administration of a DNA active ingredient in mice. The dominant peanut allergen gene (pCMVArah2) present on a plasmid DNA were formulated together with chitosan having an Mw of about 390 000 by means of complex acervation to nanoparticles with a size in the range from 100 to 200 nm. These nanoparticles were administered orally to AKR/J mice, whereupon it was possible to detect transduced gene expression in the intestinal epithelial cells. The mice treated in this way produced allergen-specific secretory IgA antibodies and serum IgG2a antibodies and showed a reduced allergen-induced anaphylaxis compared with a control group.

Leong et al (1998) describes in *Journal of Controlled Release* 53, pp. 183-193 *"DNA-polycation nanospheres as non-viral gene delivery vehicles"* gene transfer vehicles which bring about foreign gene expression in vivo in BALB/c mice. The nanospheres were produced as DNA complexes with gelatin or chitosan having a size in the range from 200 to 700 nm.

WO 02/094983 describes formulations of nucleic acids, antibodies having specificity for DNA and cationic macromolecule complexes related thereto. Formulation takes place in the form of nanoparticles, and increased transfection rates are detected both in vitro and in vivo. Formulations for oral administration with delayed release of active ingredient are mentioned.

WO 03/007313 describes oral multiparticulate pharmaceutical forms which comprise the active ingredient in the form of a multiplicity of so-called patches. A patch is a disc-shaped object made of biocompatible material having a diameter of from 500 µm to 5 mm and a height of from 100 to 1000 µm. The patch consists of two layers or sides, of one side which has only low permeability for water or body fluids, e.g. made of ethylcellulose, and of a second side which comprises the active ingredient, e.g. a protein, a polysaccharide or a small molecule, which may be present in a mixture with mucoadhesive polymers, e.g. chitosan, CMC, polyacrylic acid or pectin. The patches can be compressed to form a tablet or else be packed into a capsule which is additionally equipped with a coating soluble in intestinal juice. The active ingredient preparations may also in addition be combined with so-called enhancers such as fatty acids, fatty alcohols, esters, surface-active substances and protease inhibitors. At the site of action, e.g. in a particular segment of the intestine, the capsule dissolves and releases the patches. The released patches are able to adhere with their mucoadhesive side to the intestinal mucosa and there deliver the active ingredient in a delayed manner and directed towards the intestinal mucosa. The second, only slightly permeable side of the patches is intended to provide the active ingredient with a certain protection against chemical or enzymatic inactivation from the side facing the intestinal lumen and also to prevent the active ingredient escaping on this side.

WO 03/092732 describes pH-sensitive polymers based on anionic (meth)acrylate copolymers having a comparatively low molecular weight Mw of 1000 to 50 000. The pH-sensitive polymers are also suitable inter alia for complexing nucleic acids. The pH-sensitive polymers have cytotoxic properties only in high concentrations or not at all in the region of pH 7.0 or slightly above, but have cytotoxic or hemolytic or membranolytic effects in vivo even in low concentration below pH 6.5.

Problem and Solution

WO 99/38964 describes nucleic acids and vectors relating to the human telomerase gene and the promoter of this gene. The nucleic acids described therein may be regarded as potential active ingredients for gene therapy of tumour cells. Oral administration of the active ingredient types described in WO 99/38964 is suggested only very generally. There is a need for proposed formulations which allow a skilled person to transport active ingredients of this type to the site of action in such a way that premature inactivation, especially by nucleases, does not occur and a sufficient proportion of the active ingredient succeeds in transfecting the target cells. WO 02/094983, which was mentioned at the outset and which describes antibody-DNA conjugate complexes in nanoparticles, also gives only rather general hints for the formulation of oral pharmaceutical forms.

WO 03/007913 describes a possible solution to the provision of oral pharmaceutical forms which are released in the intestinal lumen and are intended to act there. One disadvantage of this solution may, inter alia, be regarded as being the elaborate construction and production of the two-layer patch structures. It appears particularly unfavourable for the drug form to be provided as capsule having a coating which is resistant to gastric juice and soluble in intestinal juice. With a size of distinctly more than 2.5 mm, it is to be feared that the therapeutic reproducibility will be inadequate. The time for the capsule to pass through the stomach may vary widely. In any event, a delayed onset of action is to be expected. In addition, the capsule may itself dissolve rapidly or slowly after partial dissolution of the coating. The two principles of coating and capsule overlap in an unfavourable way in this case, so that the release of the patches must be expected overall to be uncontrolled. The capsule may, in a situation where it is at least partly accessible to the intestinal juices, remain intact or else be substantially broken down mechanically, depending on the current intestinal contents or intestinal peristalsis. There may be on the one hand a sudden release of large amounts of patches, or on the other hand also an unwanted delay of release, depending on the disintegration or mechanical stress on the initially coated capsule structure. An active ingredient delivery which can overall be controlled better would therefore be desirable.

The present invention relates to pharmaceutical forms which can be administered orally for nucleic acid active ingredients, in particular for the purposes of gene therapy. A general problem in this connection is to formulate the active ingredient in a form which favours the transfection of living cells at the site of action and, at the same time, ensure that the active ingredient or at least a sufficient amount reaches the site of action in the form capable of transfection. One of the problems of the invention was regarded, as being to provide a pharmaceutical form which is suitable for targeted and efficient release of nucleic acid active ingredients. The pharmaceutical form is intended to provide high dosage reliability and be distributed well in the intestinal lumen after a rapid passage through the stomach. The contained nucleic acid active ingredient is moreover intended to be protected substantially from physical, chemical or nucleolytic inactivation and to be released at the defined site of action in such a way that a large proportion of the active ingredient can be absorbed by the body. The site of release is intended to be variably and reliably adjustable depending on the therapeutic aim. The pharmaceutical form is intended to comprise besides the DNA active ingredient only pharmacologically acceptable, nontoxic ingredients, so that no unwanted side effects are to be expected from the outset even if intake of the pharmaceutical form is frequent or regular.

The Problem is Solved by a

Oral multiparticulate pharmaceutical form comprising pellets having an average diameter in the range from 50 to 2500 µm, which are composed of
  a) an inner matrix layer comprising nanoparticles which comprise a nucleic acid active ingredient, and are embedded into a matrix of a polymer having a mucoadhesive effect, where the matrix may optionally comprise further pharmaceutically usual excipients,
  b) an outer film coating consisting essentially of an anionic polymer or copolymer which may optionally be formulated with pharmaceutically usual excipients, especially plasticizers,
    characterized in that
the multiparticulate pharmaceutical form is formulated so that the contained pellets are released in the pH range of the stomach, the outer coating is adjusted through the choice of the anionic polymer or copolymer and its formulation with excipients and its layer thickness so that the coating dissolves in pH ranges from 4.0 to 8.0 in the intestine within 15 to 60 min so that the active ingredient-containing, mucoadhesive matrix layer is exposed and can bind to the intestinal mucosa and release the active ingredient there, where the polymer having a mucoadhesive effect is chosen so that it exhibits a mucoadhesive effect of at least $\eta_b$=150 to 1000 mPa·s and a water uptake of from 10 to 750% in 15 min in a range of +/−0.5 pH units relative to the pH at which the outer coating starts to dissolve, and the active ingredient content of the nanoparticles in the matrix layer is a maximum of 40% by weight of the content of polymers having a mucoadhesive effect.

EMBODIMENT OF THE INVENTION

The invention relates to an oral multiparticulate pharmaceutical form, in particular in the form of a tablet, minitablet, pellets packed into capsules, sachets or powders for reconstitution, comprising pellets having an average size or average diameter in the range from 50 to 2500, preferably from 100 to 1000 µm, which are composed of
  a) an inner matrix layer comprising nanoparticles which comprise a nucleic acid active ingredient, and are embedded into a matrix of a polymer having a mucoadhesive effect, where the matrix may optionally comprise further pharmaceutically usual excipients,
  b) an outer film coating consisting essentially of an anionic polymer or copolymer which may optionally be formulated with pharmaceutically usual excipients, especially plasticizers.

The multiparticulate pharmaceutical form is formulated so that the contained pellets are released in the pH range of the stomach.

The term pellets in the context of the invention includes round to spherical agglomerates which may also be referred to as microparticles, beads or minitablets, as long as they have the structure and size described in the invention.

The outer coating is adjusted by the choice of the anionic polymer or copolymer or its formulation with excipients and its layer thickness so that the coating dissolves in pH ranges from 4.0 to 8.0, preferably from 5.5 to 7.8, particularly preferably 5.8 to 7.5, in the intestine within 15 to 60, preferably from 20 to 40 min, so that the active ingredient-containing mucoadhesive matrix layer is exposed and can bind to intestinal mucosa and release the active ingredient there.

The polymer or copolymer having a mucoadhesive effect is chosen so that it exhibits a mucoadhesive effect of at least $\eta_b$=150 to 1000, preferably 150 to 600 mPa·s and a water uptake of from 10 to 750, preferably 10 to 250, particularly preferably 10 to 160% in 15 min, in a range of +/−0.5, preferably +/−0.3 pH units relative to the pH at which the outer coating starts to dissolve, and the active ingredient content of the matrix layer is not more than 40, in particular from 0.001 to 15 or 0.05 to 5% by weight of the content of polymers having a mucoadhesive effect.

The Inner Matrix Layer

The inner matrix layer acts as active ingredient carrier. The inner matrix layer additionally has the function of binding the active ingredient, by means of the contained mucoadhesive polymer, to the intestinal mucosa so that the active ingredient can enter the body therefrom. The inner matrix layer additionally has the function of protecting the active ingredient from physical, chemical or enzymatic inactivation.

The inner matrix may additionally comprise pharmaceutical excipients, especially G-protein coupled receptors and ligands (see, for example, WO 02/102407, pp. 74-76), especially 8-OH-DPAT, aminoketanserin, atropine, butaclamol, chlorpromazine, chloroprozhixen, cinanserin, cyanopindolol, cyproheptadine, domperidone, epi-depride, epi-nephrine, fenoldopam, flupenthixol, fluphenazine, haloperidol, hexocyclium, himbacin, iodomelatonin, ketanserin, lysergic acid derivatives, mesoridazine, mesulergin, methoctramine, methyl-sergide, metoclopramide, mianserin, molindonem, muscarinic, naloxone, N-methylspiperone, nor-epinephrine, pergolide, phentolamine, pirenzepine, PPHT-coumarin, PPHT-rhodamine, PPHT-Texas red, prazosin, promazine, raclopride, serotonin, speperone, spriroxatrine, sulpiride, sumatriptan, tenilapine and trifluprimazine.

The inner matrix may additionally comprise penetration promoters, e.g. plasticizers such as, for example, triethyl citrate, acetyl trietyl citrate, diethyl sebacate, dibutyl sebacate, polymers such as carbomer, chitosan, chitosan-cysteine, sodium carboxymethyl-cellulose, N-trimethylated chitosan, polycarbophil-cysteine, long-chain fatty acids, their esters (for example mono- and diglycerides) and their salts such as lauric acid, laurinsulphonic acid, palmitic acid, caprylic acid, capric acid, oleic acid, acylcarnitines, chelating agents such as EDTA, salicylates, cyclodextrins, polyacrylic acids, bile acids such as cholic acid, cholyltaurine, cholylsarcosine, chenodeoxycholic acid and their salts such as Na chelate, Na glycocholate, Na taurocholate, Na taurodihydrofusidate, Na glycodihydrofusidate, surfactants and emulsifiers such as, in particular, polyethylene-660 12-hydroxy-stearate (Solutol® HS15), (Solutol® HS15), polysorbate 80 (Tween 80), polyoxyethylated castor oil (Cremophor EL), polyoxyethylene-polyoxypropylene glycol (Pluronic® F68), the toxin zonula occluders toxin (ZOT), and vitamins such as vitamin E (tocopherol) or Vitamin B12.

Pharmaceutical excipients, penetration promoters and/or G-protein coupled receptors and ligands are preferably not present in the inner matrix layer or are present in only small amounts, e.g. from 0.01 to 10, preferably 0.05 to 2, particularly preferably 0.1 to 1% by weight.

Nucleic Acid Active Ingredients

The matrix layer comprises nanoparticles having a nucleic acid active ingredient. The nucleic acid active ingredient has the task of eliciting at the target site in vivo an interaction with the DNA of mammalian cells, in particular human cells, which lead to an altered DNA structure in the cell or very generally to altered cell properties. In this connection, mention should primarily be made of so-called gene therapy, the aim of which is to repair defective gene structures in genetically related disorders. This may take the form of, for example, inactivation or switching-off of unwanted gene activities such as, for example, the telomerase activity in tumour cells. It may also take the form of a restoration of gene activities which are normally present in healthy cells, e.g. the p53 gene activity, a tumour suppressor gene which has long been known and intensively researched. The invention accordingly relates to pharmaceutical forms which can be administered orally for nucleic acid active ingredients, in particular for gene therapy.

The nucleic acid active ingredient may be a single- or double-stranded DNA (deoxyribonucleic acid) or RNA (ribonucleic acid) or a DNA-RNA chimer, it being possible for naturally occurring and/or non-naturally occurring synthetically modified nucleotides to be present. The nucleic acid active ingredient may be in linear or circular form. It may take the form of oligonucleotide units, e.g. with a length of from 10 to 200 bases or base pairs. It may also take the form of longer units of, for example, mere than 200 to 100 000, 500 to 10 000 or 1000 to 5000 bases or base pairs. Besides the sequence acting as actual active ingredient, e.g. a nucleic acid sequence which is present in the target cell or is to be supplemented, the nucleic acid active ingredient may where appropriate also comprise vector sequences which are not ordinarily present in the target cell and are not intended to interact with the latter.

Examples of known vector systems are those which are based on double-stranded DNA and are derived from plasmids or vectors based on viral systems. Known examples are recombinant adeno-associated viral vectors (rAAV). Other double-stranded vectors may comprise promoter or regulatory sequences from cytomegaloviruses (CMV) or the SV40 virus. Other vectors may be derived from single-stranded DNA which can be protected from degradation with the aid of attached RNA elements. Also known are so-called RDO I and RDO II constructs in which short DNA pieces, e.g. 30 to 60 bases, are provided on the ends with short RNA pieces of from 1 to 4 bases. The half-life or the nuclease resistance can be additionally increased by introducing non-naturally occurring nucleotides into the RNA or DNA. It is possible in this connection for, for example, single oxygen atoms to be replaced by sulphur atoms, so that phosphorus-sulphur bridges are obtained (MSO). The diversity of nucleic acid forms which are suitable as gene repair or gene replacement vectors and which can be employed as active ingredients in the context of the present invention is described for example Nature Reviews Vol. 4, 2003, pp. 679-689, Li Liu et al. Preference is given to nucleic acid fragments which comprise essentially only the nucleic acid sequence acting as active ingredient and only small proportions of or no vector DNA.

The nucleic acid active ingredient may be present in a complex or conjugate, e.g. with cationic polymers or proteins such as, for example, antibodies. The complexation or conjugate formation may take place reversibly or irreversibly covalently through chemical bridge bonding or non-covalently via van der Waal's forces, ionic linkages, hydrophobic linkage. The molecules displayed besides the nucleic acid active ingredient in the complex or conjugate themselves display no therapeutic effect, however, and are thus to be regarded as formulation aids and not as active ingredient or part of the active ingredient.

The nucleic acid active ingredient may, where appropriate, be formulated with the assistance of proteins or peptides. However, they themselves, however, display no therapeutic effect and are thus to be regarded as formulation aids and not as active ingredient or part of the active ingredient.

The nucleic acid may, for example as disclosed in WO 02/094983, be in the form of a complex with an antibody which binds specifically to the nucleic acid, and with a cationic substance. It has been possible to show that this measure can contribute to an increased transfection rate both in vitro and in vivo. Possible and preferred in this connection are monoclonal IgG antibodies or IgM antibodies which act completely or else as fragments, Fc antibody fragments, Fab' antibody fragments, F(a,b)'2 antibody fragments or half antibody fragments which, however, must in each case comprise at least one anti-DNA binding site. The molecular ratio of nucleic acid to anti-DNA antibody may be for example from 1:20 to 1:5.

The nucleic acid active ingredient may be aimed for example at the therapy of haemophilia and comprise a coagulation factor gene, e.g. the cDNA gene of human coagulation factor IX (see, for example, WO 03/028657 or Palmer et al., Blood, 1989, 73 (2), p. 438-445 or Yao et al., Proc Natl Acad Sci, USA, 1992, 89(8): pp. 3357-3361). The nucleic acid active ingredient may, besides the therapeutically effective gene portion, also comprise an immunotolerance-inducing gene such as, for example, the Fas ligand. The coexpressed Fas ligand or Fas gene section can induce apoptosis in T cells which can, after gene transfer into the target cells, be specifically activated. Vectors connected with apoptosis induction in leukaemia cells can also be inferred from Walensky et al., 2004, *"Activation of Apoptosis in Vivo by a Hydrocarbon-Stapled BH3 Helix"*, Science, 305, pp. 1466-1470.

The nucleic acid active ingredient may comprise for example a gene section, especially the promoter region, of the human telomerase gene. A suitable example is the gene therapy vector pGT62-codAupp described in WO 99/38964, or other vectors which can be inferred by a skilled person from WO 99/38964. The nucleic acid active ingredient may comprise a tumour suppressor gene section, e.g. the p53 tumour suppressor gene or fragments thereof. U.S. Pat. No. 6,451,593 B1 describes principles for constructing expression vectors for gene therapy which are suitable for producing nucleic acid active ingredients in the context of the invention.

Nanoparticles

The pharmaceutical form comprises nanoparticles which may preferably have a size in the range from 20 to 1000, preferably from 50 to 250, particularly preferably 80 to 220, in particular from 100 to 200 nm.

The nucleic acid present in the nanoparticles may preferably be present in the form of a complex with a cationic substance.

The cationic substance may be a cationic lipid, a cationic polypeptide and/or a cationic polymer. Polyethyleneimine or derivatives may also be suitable.

Cationic lipids may be for example commercial mixtures of N-[1-(2,3-dioleyloxy)propyl]-N—N—N-trimethylammonium chloride (DOTMA) and dioleylphosphatidyiethanolamine (DOPE). Suitable examples are also N-[1-(2,3-dioleyloxy)propyl]-N—N—N-trimethylammonium methyl sulphate (DOTAP), dioleylphosphatidylcholines (DOPC), dioccadecylamidoglycylspermine (DOGS).

Cationic polypeptides are preferably synthetically prepared homopolymers of amino acids with cationic side groups. Mention should be made of poly-lysine, poly-arginine, poly-ornithine and poly-histidine. The chain lengths may vary from a few units up to large units, e.g. 3 to 20, 10 to 50, 50 to 100 or up to 500 or up to 1000 amino acids. It is also possible to employ naturally occurring proteins having predominantly cationic properties such as, for example, histone proteins.

Preference is given, in relation to other substances with comparatively little pharmacological experience, to (meth) acrylate copolymers because they have been safely used for decades in medicaments administered orally. The cationic polymer may therefore preferably be a (meth)acrylate copolymer, in particular a (meth)acrylate copolymer which has tertiary or quaternary amino groups. The glass transition temperature (ISO 11357-2, subsection 3.3.3) of the cationic (meth)acrylate copolymer is preferably in the range from 40 to 60° C., and the molecular weight Mw (weight average) is from 100 000 to 200 000 (the molecular weight Mw can be determined for example by gel permeation chromatography or by a scattered light method (see, for example, H. F. Mark et al., Encyclopedia of Polymer Science and Engineering, 2nd Edition, Vol. 10, pages 1 et seq., J. Wiley, 1989). To improve the excretion via the kidney or the biliary tract, preference is given to cationic (meth)acrylate copolymers having a low molecular weight Mw, e.g. having an Mw of 50 000 or less, 5000 to 40 000, 10 000 to 30 000 or 15 000 to 25 000.

The molecular weight Mw (weight average) can be determined for example by viscometry or gel exclusion chromatography (GPC). Viscometric values (limiting viscosity number) can be determined in chloroform or in DMF (dimethylformamide) at 23° C. and should preferably be in the range from 10 to 20, preferably 11 to 15 $n_{spec/c}$ (cm$^3$/g). Viscosity numbers can be measured for example as specified in ISO 1628-6.

Particular preference is given to a (meth)acrylate copolymer which is composed of free-radical polymerized units of 20-30% by weight methyl methacrylate, 20-30% by weight butyl methacrylate and 60-40% by weight dimethylaminoethyl methacrylate. The (meth)acrylate copolymer can in particular be employed in micronized form with average particle sizes of from 10 to 30 µm. A specifically suitable commercial (meth)acrylate copolymer having tertiary amino groups is composed for example of 25% by weight methyl methacrylate, 25% by weight butyl methacrylate and 50% by weight dimethylaminoethyl methacrylate (Eudragit® E100). A micronized form (Eudragit® E PO, powder) having an average particle size of from 10 to 20 µm is particularly preferred. This form can be processed particularly well to nucleic acid-containing nanoparticles. The result in this case is an evidently particularly favourable complex formation, which may contribute to increased transfection rates, with the nucleic acid molecules.

Nanoparticles Comprising Nucleic Acid Active Ingredient and Cationic and Anionic (Meth)Acrylate Copolymers The transfection rates of the respective nucleic acids for the target cell type can be further optimized by adding, in the preparation of the nanoparticles comprising nucleic acid active ingredient and cationic (meth)acrylate copolymer, in addition an anionic (meth)acrylate copolymer in proportions of from 0.1 to 40, in particular 1 to 30, particularly preferably 2 to 25% by weight based on the nucleic acid active ingredient and the cationic (meth)acrylate copolymer. The nanoparticles must then be checked for their transfection rate in an in vitro assay with a cell culture of the target cell type, where available, or with a cell type which is at least similar or reacts similarly. It is possible in this way to adjust a suitable balance between the binding forces of the nucleic acid in the complex and its release from the complex into the living cell. If the binding effect due to one cationic (meth)acrylate copolymer alone is initially too strong, so that the transfection rate of the nucleic acid is unsatisfactorily low, the binding effect can be weakened by adding the anionic (meth)acrylate copolymer until the transfection rate reaches an optimum which is specific for the nucleic acid employed and for the target cell type. This mode of formulation has the advantage that both the cationic and the anionic (meth)acrylate copolymer are pharmacologically acceptable, so that scarcely any or no side effects are to be expected.

Suitable and preferred anionic (meth)acrylate copolymers are the same types which can also be used for the outer coating, i.e. (meth)acrylate copolymers having a content of monomers having anionic groups of from 5 to 60% by weight (Eudragit® types L, S, L100-55, FS). In many cases, a surprising increase in the transfection rates can be achieved by employing anionic (meth)acrylate copolymers composed of 20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers capable of vinylic copolymerization,
where the proportions of the monomers add up to 100% by weight, with the proviso that the glass transition temperature of the copolymer according to ISO 11357-2, subsection 3.3.3 (midpoint temperature $T_{mg}$) is from 55 to 70° C.

The abovementioned copolymer is composed in particular of free-radical polymerized units of 20 to 33, preferably 25 to 32, particularly preferably 28 to 31% by weight methacrylic acid or acrylic acid, with preference for methacrylic acid, 5 to 30, preferably 10 to 28, particularly preferably 15 to 25% by weight methyl acrylate, 20 to 40, preferably 25 to 35, particularly preferably 18 to 22% by weight ethyl acrylate, and more than 10 to 30, preferably 15 to 25, particularly preferably 18 to 22% by weight butyl methacrylate, where the monomer composition is chosen so that the glass transition temperature of the copolymer is from 55 to 70° C., preferably 59 to 66, particularly preferably 60 to 65° C.

To improve the excretion via the kidney or the biliary tract, anionic (meth)acrylate copolymers having a low-molecular weight are preferred, e.g. preferred having an $M_w$ of 50 000 or less, 5000 to 40 000, 10 000 to 30 000 or 15 000 to 25 000.

The molecular weight Mw (weight average) can be determined for example by viscometry or gel exclusion chromatography (GPC). Viscometric values (limiting viscosity number) can be determined in chloroform or in DMF (dimethylformamide) at 23° C. and should preferably be in the range from 10 to 20, preferably 11 to 15 $n_{spec/c}$ (cm$^3$/g). Viscosity numbers can be measured for example as specified in ISO 1628-6.

Anionic (meth)acrylate copolymers having a low molecular weight are pH-sensitive polymers which, in the region of pH 7.0 or slightly above, have cytotoxic properties only on high concentrations, or not at all, but below pH 6.5 have hemolytic and membranolytic effects even in low concentration in vivo. The polymers can serve as modulators of the binding strength between nucleic acid active ingredient and cationic (meth)acrylate copolymer in the nanoparticles and, at the same time, have a beneficial influence on the transfection rates. The proportion of anionic (meth)acrylate copolymers having a low molecular weight in the nanoparticles can contribute in particular to intracellular release of the nucleic acid active ingredient after uptake into endosomes through their subsequent destabilization or lysis.

Anionic (Meth)Acrylate Copolymers Having a Low Molecular Weight for Nanoencapsulation In a preferred embodiment, anionic (meth)acrylate copolymers having a low molecular weight, e.g. having an $M_w$ of 50 000 or less, 5000 to 40 000, 10 000 to 30 000 or 15 000 to 25 000, are applied by nanoencapsulation as shell to nanoparticles which comprise the nucleic acid active ingredient and cationic polymer, preferably a cationic (meth)acrylate copolymer. The proportion of anionic (meth)acrylate copolymers having a low molecular weight on the surface of the nanoparticles can contribute in particular to intracellular release of the nucleic acid active ingredient after uptake into endosomes through their subsequent destabilization or lysis. In addition, the nucleic acid active ingredient is better protected in the interior from nucleolytic degradation, so that more active ingredient can reach the target site.

Proportions of Active Ingredient

The proportion of nanoparticles in the matrix layer is preferably not more than 40, in particular 0.001 to 15 or 0.05 to 5% by weight of the content of polymer having a mucoadhesive effect. The proportion of the nucleic acid active ingredient in the nanoparticles can be for example from 1 to 50, preferably 2 to 25% by weight.

Preparation of Nanoparticles

The preparation of nanoparticles is known. Known methods are coacervation, complex formation, emulsion precipitation, evaporation of the organic solvent content from a water-in-oil emulsion, resulting in nanoparticles in the aqueous phase. Evaporation of the organic solvent content from an oil-in-water emulsion, resulting in nanoparticles in the aqueous phase. Leong et al. (1998) describes the preparation of nanoparticles in *Journal of Controlled Release* 53, pp. 183-193 *"DNA polycation nanospheres as non-viral gene delivery vehicles"*. Roy et al. (1999) describes the preparation of nanoparticles in *Nature Medicine*, Vol. 5, No, 4, pp. 387-391, *"Oral gene delivery with chitosan-DNA nanoparticles generates immunologic problems in murine model of peanut allergy"*.

Nanoencapsulation is a boundary layer polymerization method (see, for example, Chouinard F. et al., Pharm Res., 1994, June 11(6): 869-874). Nanocapsules can be generated by dispersing nanoparticles as insoluble complexes in aqueous medium, and emulsifying the dispersion in an organic solvent. The dispersion in an organic solvent comprises for example a (meth)acrylate copolymer. On evaporation of the organic solvent, the (meth)acrylate copolymer precipitates and forms a shell around the nanoparticles. Encapsulation of the nanoparticles is advantageous because an additional protection of the complexed nucleic acid active ingredient is ensured during the absorption processes by the enterocytes and the liver.

Polymers Having a Mucoadhesive Effect

The matrix layer further comprises polymers having a mucoadhesive effect. Suitable polymers having a mucoadhesive effect are in particular a chitosan (chitosan and derivatives, chitosans), (meth)acrylate copolymers consisting of 20-45% by weight methyl methacrylate and 55 to 80% by weight methacrylic acid, celluloses, especially methylcelluloses, such as Na carboxymethylcellulose (e.g. Blanose® or Methocel®). Preference is given, in relation to other substances with comparatively little pharmacological experience, to (meth)acrylate copolymers because they have been safely used for decades in medicaments administered orally.

The polymer having a mucoadhesive effect is chosen so that it displays a water uptake of from 10 to 750%, preferably 10 to 250, particularly preferably 10 to 160% in 15 min in a range of +/−0.5, preferably +/−0.3 pH units relative to the pH at which the outer coating starts to dissolve.

Measurement of the Mucoadhesive Properties

A suitable measurement method for characterizing mucoadhesive properties is contained in Hassan and Gallo (1930) (see Hassan E. E. and Gallo J. M. *"A Simple Rheological Method for the in Vitro Assessment of Mucin-Polymer Bioadhesive Bend Strength" Pharma Res.* 7(5), 491 (1990)). The method is based on the assumption that the viscosity ($\eta$, dynamic viscosity or viscosity coefficient) of a mixture of polymers with mucin is different from the total of the viscosities of the individual components. The relationship applying is $\eta_{mixture\ of\ polymer\ with\ mucin} = \eta_{mucin} + \eta_{polymer} + \eta_b$, where $\eta_b$ stands for the difference. A higher $\eta_b$ means greater mucoadhesive properties. The individual components are initially measured for their viscosity using a rotational viscometer. A 0.5% strength (w/w) aqueous solution of the mucoadhesive polymer and a 15% strength solution of porcine gastric mucin are employed. To determine the mucoadhesive properties $\eta_b$, mucin and polymer are measured alone and mixed in the stated, concentrations.

The polymer having mucoadhesive effect is chosen so that it exhibits a mucoadhesive effect measured as viscosity $\eta_b$ of from 150 to 1000, preferably 150 to 600, mPa·s in a range of +/−0.5, preferably +/−0.3 pH units relative to the pH at which the outer coating starts to dissolve.

Hydration and Water Uptake

The hydration of polymers is based on the affinity of the polymer to take up water. Polymers swell owing to this water uptake. This is concerned with an imbalance between the chemical potential of the water in the polymer and the water in the surrounding medium. The water is taken up, owing to the osmotic pressure of the polymer, until an equilibrium is reached between the inner and the outer phase. The polymer is then 100% hydrated. Polymers having a low average molecular weight are then in the form of a solution. A gel is produced with polymers having a higher molecular weight or crosslinked polymers. The water uptake until the equilibrium is set up may amount for example to up to 10 times the inherent weight, corresponding to 1000% of the polymer weight.

Measurement of the Percentage Water Uptake

Measurement of the percentage water uptake is familiar to the skilled person. A suitable method is described for example in the Lehrbuch der pharmazeutischen Technologie/Rudolf Voigt, Basel: Verlag Chemie, 5th completely revised edition, 1984, page 151, 7.7.6 under "Aufsaugvermögen". The method makes use of the so-called Enslin apparatus, in which a glass suction filter funnel is connected by tubing to a graduated pipette. The pipette is mounted exactly horizontally in such a way that it is at the same level as the glass frit. A water uptake of 100% is defined in the present case as a water uptake of 1 ml of water per 1 g of polymer having a mucoadhesive effect in 15 min.

which it would otherwise have no mucoadhesive effect or not to this extent. This has the advantage that a certain protection against nucleases whose pH optimum is in higher pH ranges can be achieved. The same principle can also be applied in the converse manner by raising the pH of the matrix by adding a base, and combining with a film coating which dissolves at lower pH values.

Examples of the Selection of Suitable Mucoadhesive Polymers

The selection of suitable mucoadhesive polymers is based on their mucoadhesive properties and their water uptake capacity. The polymers should have a mucoadhesive effect of at least $\eta_b$=150 to 1000 mPa·s and a water uptake of from 10 to 750% in 15 min in the respective pH range. The following table gives a list by way of example.

Chitosan is suitable for example for use in a surrounding pH region of pH 5.5 (duodenum) or at another surrounding pH region (ileum or colon) as long as the matrix pH region has been adjusted, e.g. with the aid of a buffer system, to the region around pH 5.5.

The (meth)acrylate copolymer listed in the table is more suitable for a pH region of pH 7.2 than for a pH region around pH 5.5.

Na alginate is suitable for the pH region around pH 5.5 but not for pH 7.2.

Na carboxymethylcellulose and crosslinked polyacrylic acid are suitable over a wide pH range from 5.5 to 7.2.

| Mucoadhesive polymer | Mucoadhesive effect $\eta_b$ [mPa·s] at pH 5.5 | Mucoadhesive effect $\eta_b$ [mPa·s] at pH 7.2 | $H_2O$ uptake [% in 15 min] at pH 5.5 | $H_2O$ uptake [% in 15 min] at pH 6.0 | $H_2O$ uptake [% in 15 min] at pH 7.2 |
|---|---|---|---|---|---|
| Chitosan | 220 | 0 | 140 | 320 | 320 |
| (Meth)acrylate copolymer* | 150 | 480 | 170 | 50 | 125 |
| Na alginate | 580 | 0 | 40 | 50 | 50 |
| Na carboxymethyl-cellulose | 300 | 250 | 55 | 50 | 50 |
| Polyacrylic acid crosslinked | 350 | 340 | 50 | 25 | 25 |

*= (meth)acrylate copolymer composed of 30% by weight methacrylate and 70% by weight methacrylic acid The comparatively rapid water uptake or hydration and the high degree of hydration ensure, at the time at which the outer coating starts to dissolve, a rapid protection of the active ingredient and a direct binding to the intestinal mucosa. Binding of the active ingredient in the mucoadhesive matrix should be only small so that the active ingredient can pass directly from the intestinal mucosa into the body.

Control of the Matrix pH

The mucoadhesive effect is pH-dependent for many mucoadhesive polymers. The pH in the matrix can be specifically controlled through the addition of an acid, of a base or of a buffer system. The inner matrix may comprise as polymer having a mucoadhesive effect for example a chitosan which is employed together with an acetate buffer system. The acetate/Na acetate buffer, e.g. adjusted to pH 5.0 to 5.5 can be present as an additive in the matrix or be applied to a core onto which the matrix is applied. It is possible in this way to employ chitosan also in combination with film coatings which start to dissolve at higher pH values, e.g. pH 6.0 to 8.0. Despite the high surrounding pH, the low pH is maintained in one microenvironment of the matrix. It is onus possible to utilize the mucoadhesive properties of the polymer in a pH range in The Outer Coating of Anionic (Meth)Acrylate Copolymers The outer coating of anionic polymers or copolymers serves as coating resistant to gastric juice in order to protect the inner matrix layer from gastric juices. The outer coating additionally acts to protect the active ingredient from nucleolytic enzymes until the time when the coating reaches a section of the intestine (duodenum, jejunum, ileum or colon) where it starts to dissolve. The outer coating serves in this case in particular for so-called "gastrointestinal targeting", i.e. the targeted release of the inner matrix layer at the sections of the intestine determined by the pH prevailing there. For there to be no impediment to delivery of the inner matrix layer, the (meth)acrylate copolymer of the outer coating should exhibit minimal or only slight interactions with the active ingredient or the mucoadhesive polymer of the inner matrix layer.

Suitable anionic polymers and copolymers are cellulose glycolate (Duodcell®), cellulose acetate phthalate (CAP, Cellulosi acetas, PhEur, cellulose acetate phthalates, NF, Aguateric®), cellulose acetate succinate (CAS), cellulose acetate trimeliate (CAT), hydroxypropyl-methylcellulose phthalate (HPMCP, HP50, HP55), hydroxypropylmethylcellulose acetate succinate (HPMCAS-LF, -MF, -HF), polyvinyl acetate phthalate (PVAP, Sureteric®), vinyl acetate-vinylpyrrolidone copolymer (PVAc, Kollidon® VA64), vinyl acetate: crotonic acid 9:1 copolymer (VAC:CRA, Kollicoat® VAC) and/or shellac. The polymers and copolymers mentioned can in many cases be formulated in a perfectly satisfactory way to allow pH-specific dissolution to be achieved.

The outer film coating particularly preferably consists essentially of (meth)acrylate copolymers having a content of monomers having anionic groups of from 5 to 60% by weight, which may optionally be formulated with pharmaceutically usual excipients, especially plasticizers. Compared with the polymers mentioned at the outset, the anionic (meth)acrylate copolymers mentioned make it possible within the scope of the invention in many cases for the pH-specific adjustment of the dissolution pH to be adjusted even more accurately and reproducibly. The handling and application is also usually regarded as less elaborate.

The (meth)acrylate copolymer for the outer coating preferably consists of 40 to 95, preferably 45 to 90, in particular 30 to % by weight of free-radical polymerized $C_1$- to $C_4$-alkyl esters of acrylic or methacrylic acid and may comprise 5 to 60, preferably 8 to 40, in particular 20 to 35% by weight (meth)acrylate monomers having an anionic group.

The proportions mentioned normally add up to 100% by weight. However, it is possible in addition, without this leading to an impairment or alteration of the essential properties, for small amounts in the region of from 0 to 10, e.g. 1 to 5% by weight of further monomers capable of vinylic copolymerization, such as, for example, hydroxyethyl methacrylate or hydroxyethyl acrylate, to be present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group may be for example acrylic acid, but preferably methacrylic acid.

Also suitable are anionic (meth)acrylate copolymers composed of 40 to 60% by weight methacrylic acid and 60 to 40% by weight methyl methacrylate or 60 to 40% by weight ethyl acrylate (Eudragit® L or Eudragit® L100-55 types). The glass transition temperature (ISO 11357-2, subsection 3.3.3) of this type is in the range from 105 to 160° C., and the molecular weight Mw is 100 000 to 300 000 (the molecular weight Mw can be determined for example by gel permeation chromatography or by a scattered light method (see, for example, H. F. Mark et al., Encyclopedia of Polymer Science and Engineering, 2nd Edition, Vol. 10, pages 1 et seq., J. Wiley, 1989).

Eudragit® L is a copolymer of 50% by weight methyl methacrylate and 50% by weight methacrylic acid. This (meth)acrylate copolymer is particularly suitable for dissolution in pH ranges around pH 6.0 to 6.5 (jejunum).

Eudragit® L100-55 is a copolymer of 50% by weight ethyl acrylate and 50% by weight methacrylic acid. Eudragit® L 30D-55 is a dispersion comprising 30% by weight Eudragit® L 100-55. This (meth)acrylate copolymer is particularly suitable for dissolution in pH ranges around pH 5.5 to 6.0 (duodenum).

Likewise suitable are anionic (meth)acrylate copolymers composed of 20 to 40% by weight methacrylic acid and 80 to 60% by weight methyl methacrylate (Eudragit® S type), This (meth)acrylate copolymer is particularly suitable for dissolution in pH ranges around pH 6.5 to 7.0 (jejunum or ileum). The glass transition temperature of this type is in the range from 140 to 180° C., and the molecular weight $M_w$ is 100 000 to 150 000.

Particularly suitable (meth)acrylate copolymers are those consisting of 10 to 30% by weight methyl methacrylate, 50 to 70% by weight methyl acrylate and 5 to 15% by weight methacrylic acid.

Eudragit® FS type is a copolymer of 25% by weight methyl methacrylate, 65% by weight methyl acrylate and 10% by weight methacrylic acid. Eudragit® FS 30 D is a dispersion comprising 30% by weight of the FS type copolymer. This (meth)acrylate copolymer is particularly suitable for dissolution in pH ranges around pH 7.0 to 7.8 (ileum or colon).

Additionally suitable is a copolymer composed of
20 to 34% by weight methacrylic acid and/or acrylic acid,
20 to 69% by weight methyl acrylate and
0 to 40% by weight ethyl acrylate and/or, where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable are copolymers composed of
20 to 33% by weight methacrylic acid and/or acrylic acid,
5 to 30% by weight methyl acrylate and
20 to 40% by weight ethyl acrylate and
more than 10 to 30% by weight butyl methacrylate and, where appropriate
0 to 10% by weight further monomers capable of vinylic copolymerization,
where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and
more than 10 to 30, preferably 15 to 25, particularly preferably 18 to 22% by weight butyl methacrylate,
where the monomer composition is chosen so that the glass transition temperature of the copolymer is from 55 to 70° C. preferably 51 to 66, particularly preferably 60 to 65° C.

It is also possible to employ mixtures of the copolymers mentioned in order to adjust specific release profiles or release sites.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

The copolymers are obtained in a manner known per se by free-radical bulk, solution, bead or emulsion polymerization. They must before processing be brought to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Copolymer Preparation

All the (meth)acrylate copolymers mentioned can be obtained by free-radical polymerization of the monomers in the presence of polymerization initiators and molecular weight regulators by means of block, bead or emulsion polymerization and discharge of the polymer (see, for example, EP 0 704 207 A2, EP 0 704 208 A2 or WO 03/092732). The (meth)acrylate copolymers can be prepared in a manner known per se by free-radical emulsion polymerization in aqueous phase in the presence, of preferably anionic emulsifiers, for example by the process described in DE-C 2 135 073. Further preparation processes which are also suitable in principle are group transfer polymerization (GTP) or atom transfer radical polymerization (ATRP) (see, for example, Matyjaszewski, K. et al., Chem. Rev. 2001, 101, 2921-2990). The resulting polymer structures are random copolymers or block copolymers.

Preference is given to emulsion polymerization in the presence of from 2 to 15% by weight molecular weight regulators, an emulsifier content in the range from 0.1 to 2% by weight, a polymerization initiator quantity in the range from 0.02 to 0.4% by weight and at temperatures from 65 to 90° C. Preference is given to an emulsifier mixture, preferably composed of sodium lauryl sulphate, e.g. 0.1 to 0.5% by weight, and polyoxyethylene-20 sorbitan monooleate, e.g. 0.4 to 1.5% by weight. Particularly suitable initiators are sodium peroxodisulphate or ammonium peroxodisulphate. It is possible in this way to prepare for example a dispersion with a solids content of from 20 to 40% by weight, and to isolate the copolymer by spray drying or by coagulation and expulsion of the water in an extruder. The polymer is subsequently dissolved, preferably in an organic solvent, purified by multiple dialysis against water, and preferably freeze dried.

Examples which may be mentioned of polymerization initiators are: azo compounds such as 2,2'-azobis(isobutyronitrile) or 2,2'-azobis(2,4-dimethylvaleronitrile), redox systems such as, for example, the combination of tertiary amines with peroxides or preferably peroxides (cf. in this connection for example H. Rauch-Puntigam, Th. Völker, "Acryl-und Methacrylverbindungen", Springer, Heidelberg, 1967 or Kirk-Othmer, Encyclopedia of Chemical Technology, Vol. 1, pages 386 et sec., J. Wiley, New York, 1978). Examples of suitable peroxide polymerization initiators are dilauroyl peroxide, tert-butyl peroctoate, tert-butyl perisononanoate, dicyclohexyl peroxydicarbonate, dibenzoyl peroxide or 2,2-bis(tert-butylperoxy)butane.

The polymerization can also preferably be carried out with a mixture of different polymerization initiators differing in half life, for example dilauroyl peroxide and 2,2-bis(tert-butylperoxy)butane, in order to keep the flow of free radicals constant during the polymerization and at different polymerization temperatures. The employed amounts of polymerization initiator are generally from 0.01 to a maximum of 1% by weight based on the monomer mixture.

The molecular weights Mw can be adjusted by polymerizing the monomer mixture in the presence of molecular weight regulators. Suitable molecular weight regulators are in particular mercaptans such as, for example, n-butyl mercaptan, n-dodecyl mercaptan, 2-mercaptoethanol or 2-ethylhexyl thioglycolate, the molecular weight regulators generally being employed in amounts of from 0.05 to 15% by weight based on the monomer mixture, preferably in amounts of from 0.1 to 10% by weight and particularly preferably in amounts of from 2 to 12% by weight on the monomer mixture (cf. for example H, Rauch-Puntigam, Th. Völker, "Acryl-und Methacrylverbindungen", Springer, Heidelberg, 1967; Houben-Weyl, Methoden der organischen Chemie, Vol. XIV/1, page 66, Georg Thieme, Heidelberg, 1961 or Kirk-Othmer, Encyclopedia of Chemical Technology, Vol. 1, pages 296 et seq., J. Wiley, New York, 1978). The molecular weight regulator preferably employed is n-dodecyl mercaptan or 2-ethylhexyl thioglycolate. Ethylhexyl thioglycolate has the advantage that the hydrophobicity of the (meth)acrylate copolymer can be influenced, because the regulator is incorporated terminally into the molecule. Preferred amounts employed are 5 to 15% by weight dodecyl mercaptan or 2 to 10% by weight 2-ethylhexyl thioglycolate.

Organic Solution

The (meth)acrylate copolymers mentioned can be provided in the form of an organic solution, e.g. in a concentration of from 10 to 30% by weight. Solvents which may be used are, for example, acetone, isopropanol or ethanol or mixture thereof, which may where appropriate comprise water in proportions up to about 10% by weight. However, aqueous dispersions are preferred.

Dispersions

The (meth)acrylate copolymers mentioned can be produced and used as emulsion polymers, preferably in the form of a 10 to 50 percent by weight, in particular 20 to 40 percent strength aqueous dispersion. A solids content of 30% by weight is preferred as commercial form. Partial neutralization of the methacrylic acid units can be dispensed with for processing; it is, however, possible, for example to an extent of up to 5 or 10 mol %, if stabilization or thickening of the coating composition dispersion is desired. The weight average size of the latex particles is usually from 40 to 100 nm, preferably 50 to 70 nm, thus ensuring a viscosity of below 1000 mPa·s which is favourable for processing.

With higher degrees of neutralization, e.g. 10 to 50 mol %, or complete neutralization it is possible to convert the copolymer into a dissolved state.

In order to prepare a solution of the anionic copolymer, it is usually necessary to neutralize the acidic groups partly or completely. The anionic copolymer may for example be stirred gradually into water in a final concentration of from 1 to 40% by weight and at the same time be partly or completely neutralized by adding a basic substance such as, for example, NaOH, KOH, ammonium hydroxide or organic bases such as, for example, triethanolamine. It is also possible to employ a powder of the copolymer to which a base, e.g. NaOH, has been added during its preparation for the purpose of (partial) neutralization, so that the powder is a polymer which is already (partly) neutralized. The pH of the solution is usually above 4, e.g. from 4 to about 7.

The dispersion can for example also be spray dried or freeze dried in a manner known per se and be provided in the form of a redispersible powder (see, for example, EP-A 0 262 326). Alternative processes are freeze drying or coagulation and squeezing out of the water in an extruder with subsequent granulation (see, for example, EP-A 0 683 028).

It has surprisingly been found that copolymer dispersions from spray- or freeze-dried and redispersed powders exhibit increased shear stability. This is advantageous in particular in the case of spray application. This advantage is particularly evident when the copolymer present in the dispersion is partly neutralized to the extent of 2 to 10 mol % (based on the acidic groups present in the copolymer). Partial neutralization by adding NaOH is preferred for this purpose. An anionic emulsifier is preferably present in an amount of from 0.1 to 2% by weight. Sodium lauryl sulphate is particularly preferred as emulsifier.

Layer Thicknesses

The layer thickness of the outer coating is preferably in the range from 20 to 200, preferably from 50 to 120 µm.

Production of a Multiparticulate Pharmaceutical Form

The invention additionally relates to a process for producing a multiparticulate pharmaceutical form by
a) formulating a nucleic acid active ingredient with excipients in a manner known per se to nanoparticles,
b) producing an inner matrix layer comprising the nucleic acid active ingredient in the form of nanoparticles and a polymer having a mucoadhesive effect and, where appropriate, further pharmaceutically usual excipients by means of spray application onto a core or by rotagglomeration, precipitation or spray processes without a core and subsequently
c) applying an outer film coating consisting essentially of an anionic polymer, which may optionally be formulated with pharmaceutically usual excipients, especially plasticizers, by spray application so that active ingredient-containing enveloped pellets are obtained, and
d) processing the resulting pellets by means of pharmaceutically usual excipients and in a manner known per se to a multiparticulate pharmaceutical form, in particular to pellet-containing tablets, minitablets, capsules, sachets or powders for reconstitution, which are formulated so that the contained pellets are released in the pH range of the stomach.

Production of Pre-Pellets and Pellets

The pelleting can take place onto active ingredient-free beads (nonpareilles), or core-free pellets can be produced.

Firstly, active ingredient-containing nanoparticles are produced.

Subsequently, the inner matrix layer is produced with or without core. This as yet uncoated, rounded layer can be referred to as pre-pellet (pellet core).

It is possible by means of a fluidized bed process to apply a solution or suspension of the mucoadhesive polymer comprising the nanoparticles having the nucleic acid active ingredient to placebo pellets or other suitable carrier materials, with evaporation of the solvent or suspending agent. The production process can be followed by a drying step.

The nucleic acid active ingredient is introduced in the form of nanoparticles having the polymer having a mucoadhesive effect into an organic solvent or into water, and mixed. In order to ensure satisfactory sprayability of the mixture, it is usually necessary to formulate a mixture of low viscosity. It may be beneficial for this purpose to employ the polymer having a mucoadhesive effect in comparatively low concentrations, e.g. from 1 to a maximum of 10, preferably 2 to 5% by weight. Addition of a detergent, e.g. Tween, in concentrations of from 0.1 to 20, preferably 0.5 to 10% by weight may moreover be advantageous to reduce the surface tension.

Besides the active ingredient it is possible for further pharmaceutical excipients to be present: binders such as cellulose and its derivatives, polyvinylpyrrolidone (PVP), humectants, disintegration promoters, lubricants, disintegrants, (meth) acrylates, starch and its derivatives, sugars, solubilizers or others.

Appropriate application processes are disclosed for example in Bauer, Lehmann, Osterwald, Rothgang, "Überzogene Arzneiformen" Wissenschafcliche Verlaqs-gesellschaft mbH Stuttgart, chapter 7, pp. 165-196.

Details are furthermore disclosed to the skilled person from textbooks. See, for example:

Voigt, R. (1984): Lehrbuch der pharmazeutischen Technologie; Verlag Chemie Weinheim—Beerfield Beach/Florida—Basel.

Sucker, H., Fuchs, P., Speiser, P.: Pharmazeutische Technologie, Georg Thieme Verlag Stuttgart (1991), in particular chapters 15 and 16, pp. 626-642.

Gennaro, A., R. (Editor), Remington's Pharmaceutical Sciences, Mack Publishing Co., Easton Pa. (1985), chapter 86, pp. 1567-1573.

List, P. H. (1982): Arzneiformenlehre, Wissen-schaftliche Verlagsgesellschaft mbH, Stuttgart.

The inner matrix can also be produced without the assistance of an inert core (nonpareilles). The ingredients of the inner matrix may in this case be rounded to as yet uncoated pellets (pre-pellets) of defined size, e.g. 50 to 1000 µm, by processes such as rotagglomeration, precipitation or spray processes, especially ultrasound fluidized spray processes. This has the advantage that the entire core volume is available for loading with active ingredient. The loading with active ingredient can thus be increased further compared with the embodiment having an inert core.

After production of the inner matrix cores (or of the pre-pellets; they are in turn provided, preferably in the spray process, with the outer coating, to result in finished pellets. The pellets are produced by spray application from organic solution, or preferably from aqueous dispersions. It is decisive for implementation in this case that uniform, pore-free coatings are produced.

Topcoat

The pellets can be provided additionally with pigmented coatings which, however, must not influence the dissolution pH. Suitable examples are coatings composed of pigmented hydroxypropylmethylcellulose or other polymers which are soluble in water or rapidly disintegrate in water.

Pharmaceutically Usual Excipients

Usual excipients or additives can be added to the formulations of the invention during production. It is, of course, always necessary for all the substances employed to be toxicologically acceptable and useable in particular in medicaments without a risk for patients.

The amounts employed and the use of the usual additives in medicament coatings or layerings are familiar to the skilled person. Possible examples of usual additives are plasticizers, release agents, pigments, stabilizers, antioxidants, pore formers, penetration promoters, gloss agents, aromatizing substances, detergents, lubricants or flavourings. They serve as processing aids and are intended to ensure a reliable and reproducible production process and good long-term storage stability, or they achieve additional advantageous properties in the pharmaceutical form. They are added to the polymer preparations before the processing and may influence the permeability of the coatings, it being possible to utilize this where appropriate as additional control parameter.

Release Agents:

Release agents usually have lipophilic properties and are usually added to the spray suspensions. They prevent agglomeration of the cores during the film coating. Talc, Mg stearate or Ca stearate, ground silica, kaolin or nonionic emulsifiers having an HLB of between 3 and 8 are preferably employed. The usual amounts employed of release agent in the coating agents and binders of the Invention are between 0.5 to 100% by weight based on the copolymer.

Pigments

Pigments incompatible with the coating agent are in particular those pigments which, if added directly to the (meth) acrylate copolymer dispersion, e.g. by stirring in, in the usual amounts used of, for example, 20 to 400% by weight based on the dry weight of the (meth)acrylate copolymer lead to destabilization of the dispersion, coagulation, to signs of inhomogeneity or similarly unwanted effects. The pigments to be used are moreover of course non-toxic and suitable for pharmaceutical purposes. Concerning this, see also, for example: Deutsche Forschungsgemeinschaft, *Farbstoffe für Lebensmittel*, Harald Boldt Verlag K G, Boppard (1978); Deutsche Lebensmittelrundschau 74, No. 4, p. 156 (1978); Arzneimittelfarbstoffverordnung AmFarbV of Aug. 25, 1980.

Pigments incompatible with the coating agent may be for example alumina pigments. Examples of incompatible pigments are orange yellow, cochineal red lake, coloured pigments based on alumina or azo dyes, sulphonic acid dyes, orange yellow S (E110, C.I. 15985, FD&C Yellow 6), indogo carmine (E132, C.I. 73015, FD&C Blue 2), tartrazine (E 102, C.I. 19140, FD&C Yellow 5), ponceau 4R (E 125, C.I. 16255, FD&C Cochineal Red A), quinoline yellow (E 104, C.I. 47005, FD&C Yellow 10), erythrosine (E127, C.I. 45430, FD&C Red 3), azorubine (E 122, C.I. 14720, FD&C Carmoisine), amaranth (E 123, C.I. 16185, FD&C Red 2), acid brilliant green (E 142, C.I. 44090, FD&C Green S).

The E numbers indicated for the pigments relate to an ED numbering. Concerning this, see also "Deutsche Forschungsgemeinschaft, Farbstoffe, für Lebensmittel, Harald Boldt Verlag K G, Boppard (1978); Deutsche Lebensmittelrundschau 74, No. 4, p. 156 (1978); Arzneimittelfarbstoffverordnung AmFarbV of Aug. 8, 1980. The FD&C numbers relate to the approval in Food, Drugs and Cosmetics by the U.S. Food and Drug Administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Plasticizers

Further additives may also be plasticizers. The usual amounts are between 0 and 60, preferably 2 to 20, in particular 5 to 10% by weight.

Plasticizers may influence the functionality of the polymer layer, depending on the type (lipophilic or hydrophilic) and added amount. Plasticizers achieve through physical interaction with the polymers a reduction in the glass transition temperature and promote film formation, depending on the added amount. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12 000. Preferred plasticizers are triethyl citrate (TEC) and acetyl triethyl citrate (ATEC). Mention should additionally be made of esters which are usually liquid at room temperature, such as citrates, phthalates, sebacates or castor oil. Esters of citric acid and sebacic acid are preferably used.

Addition of, plasticizer to the formulation can take place in a known manner, directly, in aqueous solution or after thermal pretreatment of the mixture. It is also possible to employ mixtures of plasticizers.

Production of Multiparticulate Pharmaceutical Forms

The active ingredient-containing coated pellets can be processed by means of pharmaceutically usual excipients and in a manner known per se to multiparticulate pharmaceutical forms, in particular to pellet-containing tablets, minitablets, capsules, sachets or powders for reconstitution, which are formulated such that the contained pellets are released in the pH range of the stomach. The preparation as multiparticulate pharmaceutical form places a high dosage reliability offers the advantage of good distribution of the pellets in the intestinal lumen. The multiparticulate pharmaceutical form of the invention may additionally also comprise different pellet types with different active ingredients and/or different pellet structure.

Compressed Tablets

The production of multiparticulate pharmaceutical forms by compression of a pharmaceutically usual binder with active ingredient-containing particles is described for example in Beckert et al. (1996), "Compression of enteric-coated pellets to disintegrating tablets", *International Journal of Pharmaceutics* 143, pp. 13-23, and in WO 96/01624.

Film coatings of active ingredient-containing pellets are normally applied in fluidized bed apparatuses. Film formers are normally mixed with plasticizers and release agents by a suitable process. It is possible in this case for the film former to be in the form of a solution or suspension. The excipients for film formation may likewise be dissolved or suspended. Organic or aqueous solvents or dispersing agents can be used. Stabilizers can be used additionally to stabilize the dispersion (example: Tween 80 or other suitable emulsifiers or stabilizers).

Examples of release agents are glycerol monostearate or other suitable fatty acid derivatives, silica derivatives or talc. Examples of plasticizers are propylene glycol, phthalates, polyethylene glycols, sebacates or citrates, and other substances mentioned in the literature.

A separating layer can be applied between active ingredient-containing and intestine-soluble copolymer layer and serves to separate active ingredient and coating material for the purpose of preventing interactions. This layer may consist of Inert film formers (e.g. HPMC, HPC or (meth)acrylic acid copolymers) or, for example, talc or another suitable pharmaceutical substances. It is likewise possible to use combinations of film formers and talc or similar substances. It is also possible to apply a separating layer composed of partially or completely neutralized, (meth)acrylate copolymer dispersions.

The separating layer may also consist of the same or a different mucoadhesive polymer as in the underlying matrix layer. Possible interactions or incompatibilities of the active ingredient or of the mucoadhesive polymer with the film-forming (meth)acrylate copolymer layer can be countered in this way.

Mixtures for producing tablets composed of coated particles are prepared by mixing the pellets with suitable binders for tableting, if necessary adding disintegration-promoting substances and if necessary adding lubricants. The mixing can take place in suitable machines. Unsuitable mixers are those leading to damage to the coated particles, e.g. ploughshare mixers. To achieve suitable short disintegration times it may be necessary to add the excipients to the coated particles in a specific sequence. It is possible by premixing with the coated particle with the lubricant or mould release agent magnesium stearate for its surface to be rendered hydrophobic and thus adhesion to be avoided.

Mixtures suitable for tableting normally comprise 3 to 15% by weight of a disintegration aid, e.g. Kollidon C L and, for example, 0.1 to 1% by weight of a lubricant and mould release agent such as magnesium stearate. The proportion of binder is determined by the required proportion of coated particles.

Examples of typical binders are Cellactose®, microcrystalline cellulose, calcium phosphates, Ludipress®, lactose or other suitable sugars, calcium sulphates or starch derivatives. Substances of low bulk density are preferred.

Typical disintegration aids (disintegrants) are crosslinked starch derivatives or cellulose derivatives, and crosslinked polyvinylpyrrolidone. Cellulose derivatives are likewise suitable. It is possible to dispense with the use of disintegration aids through selection of a suitable binder.

Typical lubricants and mould release agents are magnesium stearates or other suitable salts of fatty acids or substances detailed in the literature for this purpose (e.g. lauric acid, calcium stearate, talc, etc.). It is possible to dispense with the use of a lubricant and mould release agent in the mixture on use of suitable machines (e.g. tablet press with external lubrication) or suitable formulations.

It is possible where appropriate to add an aid to the mixture to improve the flow (e.g. colloidal silica derivatives, talc, etc.).

The tableting can take place on usual tablet presses, eccentric or rotary tablet presses, with compressive forces in the range from 5 to 40 kN, preferably 10-20 kN. The tablet presses can be equipped with systems for external lubrication. Special systems for die filling, which avoid die filling by means of impeller paddles, are employed where appropriate.

Further Multiparticulate Pharmaceutical Forms

As alternative to compressed tablets or minitablets, it is also possible for the active ingredient-containing coated pellets to be processed to any other orally administered multiparticulate pharmaceutical form. The coated pellets can, for example, be packed into capsules, e.g. gelatin capsules, or formulated to sachets or powders for reconstitution.

ADVANTAGEOUS EFFECTS OF THE INVENTION

The pharmaceutical form of the invention is suitable for targeted and efficient release of nucleic acid active ingredients. The pharmaceutical form exhibits a high dosage reliability and distributes well in the stomach and in the intestinal lumen. The contained nucleic acid active ingredient is moreover substantially protected from physical or nucleolytic inactivation and can be released at the defined site of action in such a way that a high proportion of the active ingredient can be taken up by the body. The pharmaceutical form therefore makes do with less active ingredient, because only a little of the active ingredient is lost. The risk of side effects is reduced overall by the targeted delivery. The site of action can be adjusted variably, depending on the therapeutic aim. The timing of the active ingredient uptake can thus be better controlled. Because the pharmaceutical form is for oral use it is accepted better overall by patients (patient compliance) compared with other administration forms. A large number of nucleic acid active ingredients can thus be made available for oral use. The risks of administration are often less than with parenteral administration in particular. The costs of administration can also be kept low because no skilled staff are necessary for the administration.

Lipophilic Matrix

An special aspect of the invention emerges when the active ingredient is incorporated in the form of nanoparticles into a lipophilic matrix which has a melting point above 37° C., preferably above 45° C., particularly preferably above 55° C., and the active ingredient-containing lipophilic matrix is incorporated into the matrix composed of the polymer having a mucoadhesive effect. The aim of formulation in the lipophilic matrix is to improve the solubility and the bioavailability of the active ingredient, preferably of sparingly or slightly soluble active ingredients (as defined in DAB 10, 2003).

A lipophilic matrix means in the context of the invention a substance or a mixture of substances in which the active ingredient can be dissolved, suspended or emulsified. The substance or the substances of the lipophilic matrix are different from the usual pharmaceutical excipients and the polymer having a mucoadhesive effect. The substance or the substances of the lipophilic matrix preferably have a hydrophobic or else amphiphilic character. The lipophilic matrix might also be referred to as amphiphilic matrix or as lipoidal matrix.

The lipophilic matrix may consist of a single substance, e.g. of a lipid, or of a mixture of substances, e.g. of a mixture of lipids. In the case of mixtures, the properties described hereinafter for water solubilities according to DAB 10, partition coefficients and/or HLB values are calculated in each case from the arithmetic mean of the parts by weight and the values of the substances of the mixture. The employed substances must not be toxic.

Lipophilic Matrix/Polymers Having a Mucoadhesive Effect

In a preferred embodiment, possible interactions of the lipophilic matrix with the polymer having a mucoadhesive effect are taken into account. In order to avoid uncontrollable interactions, the substance or the substances which form the lipophilic matrix, and the polymer having a mucoadhesive effect should preferably either have the same ionic properties, i.e. both should have concordantly either at least predominantly cationic or concordantly anionic character. In the event that substances having opposed ionic properties are selected, the polymer having a mucoadhesive effect should preferably be present in at least 50, particularly preferably 100%, neutralized form. The neutralization can take place by adding acid or base in a known manner.

Substance or Substances for Assembling the Lipophilic Matrix

The lipophilic matrix preferably consists of 80 no 100, preferably 90 to 100, particularly preferably 100% by weight of a substance or of a mixture of substances having an (averaged) HLB of from 0 to 15, preferably 2 to 10 consists. The lipophilic matrix may comprise 0 to 20, preferably 0 to 10% by weight of pharmaceutically usual excipients, especially stabilizers, thickeners or adsorbents. It is particularly preferred for no pharmaceutically usual excipients to be present.

The substance or the substances which form the lipophilic matrix may for example belong to the group of oils, fats, mono-, di- or triglycerides, fatty acids, fatty alcohols, especially $C_6$ to $C_{20}$ fatty acid, and/or a $C_6$ to $C_{20}$ alcohol including their salts, ether, ester or amide derivatives, phospholipids, lecithins, emulsifiers, lipoids, lipid-soluble vitamins or surfactants.

The lipophilic matrix may comprise for example one of the following lipid preparations; (Imwitor 308) glyceryl monocaprylates having a monoester content of >80%, (Imwitor 312) glyceryl monolaurates having a monoester content of >90%, (Imwitor 491) glycerol monostearates ($C_{16}$+$C_{18}$) having a monoester content of >90%, (Imwitor 900 P) glycerol monostearate having a monoester content of 40-55% and a $C_{18}$ content of 40-60%, (Imwitor 900 K) glycerol monostearate, having a monoester content of 40-55% and a $C_{18}$ content of 60-80%, (Imwitor 742) medium chain-length $C_8$ and $C_{10}$ glycerides having a monoester content of 45-55%, (Imwitor 928) partial glycerides of saturated vegetable $C_{10}$-$C_{18}$ fatty acids having a main content of $C_{12}$, and having a monoester content of 34-36%, $C_8$ and $C_{10}$ glycerides, Na caprylate or Na capriate.

The lipophilic matrix may comprise for example one of the following lipid preparations:

fats such as mono-, di-, triglycerides of saturated and unsaturated fatty acids and mixtures thereof. In particular glycerol stearic acid ester, glycerol palmitic acid ester, glycerol myristic acid ester, glycerolpalmitic acid stearic acid ester, glycerol lauric acid ester, glycerol caprylic acid ester, glycerol oleic acid ester, examples of these esters are Imwitor®-308, -312, -491, -742, -900, -928, -988, and Geiucire® 44/14, -50/13, Geleol, Compritol E ATO, Dynasan 114, Softisan, Witepsol, Dynacet 212, coconut fat, oils such as, for example, castor oil, sesame oil, sunflower oil, cottonseed oil, corn oil, almond oil, peanut oil, olive oil, coconut oil, carrot oil, wheat germ oil, walnut oil, neutral oils such as isopropyl myristate, isopropyl palmitate, isopropyl stearate, medium chain-length triglycerides (Miglyol®).

Short-chain aliphatic and aromatic carboxylic esters such as, for example, dibutyl phthalate, diethyl sebacate, dibutyl sebacate, tributyl citrate, acetyl tributyl citrate, glycerol triacetate, waxes such as, for example, carnauba wax, beeswax, wool wax glycerol behenic acid ester, fatty acid amides such as, for example, stearamide, palmitamide, lauramide, aliphatic long-chain carboxylic acids such as, for example, stearic acid, palmitic acid, lauric acid, myristic acid, oleic acid, caprylic acid, linoleic acid, linolenic acid. And, for example, their Ma, Al and Mg salts, fatty alcohols such as, for example, stearyl alcohol, lauryl alcohol, cetyl alcohol, myristin alcohol, glycerol formal, W/O emulsifiers such as, for example, cholesterol, glycerol monostearate, ethylene glycol monostearate, sorbitan monooleate (Span® 80), sorbitan monopalmitate (Span® 40), sorbitan monolaurate (Span® 20), sorbitan monostearate (Span® 60), sorbitan trioleate (Span® 85), sorbitan tristearate (Span® 65), sorbitan sesquioleates (Arlacel® 83), Ca, Al, Mg stearate, polyoxyethylene sorbitan tristearate (Tween® 65), polyoxyethylene sorbitan trioleate (Tween® 85), nonionic O/W emulsifiers such as, for example, macrogol stearate 400 (Chremophor® A), macrogol lauryl ether, polyethylene glycol 20 sorbitan monolaurate, sorbitan monostearate, sorbitan monopalmitate, sorbitan monooleate, macrogol 1500 glycerol triricinoleate, macrogol glycerol hydroxystearate (Cremophor® RH), macrogol 1000 glycerol monolaurate, monostearate, monooleate, sucrose monostearate. Polysorbate 60 (Tween® 60), polyoxyethylene monostearate (Myrj 49), polysorbate 80 (Tween® 80), polysorbate 40 (Tween® 40), polysorbate 20 (Tween® 20), poloxamer 407 (Lutrol® F 127), poloxamer 188 (Lutrol® F 68), polyoxyethylene ricinoleate (Cremophor® EL), polyoxyethylene 5 stearyl stearate, ionic O/W emulsifiers such as, for example, cetylstearyl sulphate (Lanette® E), Na lauryl sulphate (Texapon® Z), Na glycocholate, hederagenin, amphiphilic emulsifiers such as, for example, egg phosphatidylcholine (egg lecithin), soya phosphatidyl-choline (soya lecithin), betaine, sulphobetaines, ceramides (sphingomyelin), vitamins such as, for example, retinol (vitamin A), cholecalciferol (vitamin D), alpha-tocopherol and alpha-tocopherol acetate (vitamin E), phylloquinone (vitamin K), further excipients are gallactolipids such as, for example, monogalactosyl diacylglycerol, digalactosyl diacylglycerol, trigalactosyl diacyl glycerol, and aromatic oils such as, for example, aniseed oil, citronella oil, eucalyptus oil, fennel oil, chamomile oil, cardamom oil, pine needle oil, caraway oil, dwarf pine oil, lavender oil, mint oil, muscat oil, clove oil, peppermint oil, rosemary oil, sage oil and terpenes such as, for example, menthol, linalool, 1,4-cineol, pyrethrin, borneol, eudesmol, phytol, manool, azadirachtin, nimbin.

The content of the active ingredient-containing lipid matrix in the inner matrix layer a) can be from 1 to 60, preferably 10 to 20% by weight.

The lipophilic matrix preferably comprises at least 50% by weight glycerol monocaprylate, up to 10% by weight Na chelate, up to 10% by weight tocopherol succinate, 1 to 5% by weight of an efflux pump inhibitor in the case where the active ingredient is a substrate of the PgP efflux pump, e.g. Solutol HS 15, a triglyceride, in particular tristearate, with the components adding up to 100%. This lipophilic matrix can be incorporated directly into the mucoadhesive polymer or be emulsified in water and incorporated into the mucoadhesive polymer. In the latter case, the aqueous phase may comprise a weak acid such as, for example, citric acid.

Process

The invention also relates to a process for producing a multiparticulate pharmaceutical form with the steps a) production of the active ingredient-containing lipophilic matrix by suspending the nanoparticles comprising the nucleic acid active ingredient with the substance(s) which form the lipophilic matrix and, where appropriate, further pharmaceutically usual excipients by vigorously mixing or melting the ingredients, b) production of pre-pellets (pellet cores) by spray application of the mucoadhesive polymer mixed with the active ingredient-containing lipophilic matrix onto a core or by rotagglomeration, precipitation or spray processes without a core, c) production of pellets by spray application of a coating of the anionic polymer or copolymer, which may optionally comprise admixtures of pharmaceutically usual excipients, especially plasticizers and release agents, from a dispersion or organic solution onto the pre-pellets from step b), d) production of a multiparticulate pharmaceutical form by filling or incorporating the pellets from step c) in a manner known per se, where appropriate with use of pharmaceutically usual excipients, in particular by processing to pellet-containing tablets, minitablets, capsules, sachets or powders for reconstitution.

Preferred Process

Process steps a) and b) are preferably carried out as follows:

a) production of the inner matrix layer by preparing an emulsion or suspension of the nanoparticles comprising the nucleic acid active ingredient with the substance(s) for the lipophilic matrix, and where appropriate further pharmaceutically usual excipients by vigorously mixing the ingredients in water and producing an oil-in-water preparation having an average particle size of not more than 60, preferably not more than 20 μm, b) production of pre-pellets by spray application of the oil-in-water preparation from step a) onto the mucoadhesive polymer which may optionally comprise admixtures of further pharmaceutically usual excipients, where the ingredients are in the form of a micronized powder, e.g. having an average particle size of from 10 to 100 μm, by rotagglomeration, extrusion or granulation.

EXAMPLES

The examples illustrate procedures typical for the invention

Example 1

Preparation of Nanoparticles Comprising a Cationic (Meth)Acrylate Copolymer 2 mg of DNA (nucleic acid active ingredient), e.g. a gene therapy vector composed of double-stranded plasmid DMA having, for example, 3 000 to 10 000 base pairs, comprising a gene which is to be expressed in human cells and intended to have a therapeutic effect, is dissolved in 4 ml of phosphate buffer of pH 7.4, and mixed with 2 ml of a mouse monoclonal anti-human DNA IgM solution (1 mg/ml) and incubated at 37° C. for 1 hour. Then 1 ml of Lipofectin™ or preferably 3 ml (1 mg/ml) of modified Eudragit® E ((meth)acrylate copolymer of 25% by weight methyl methacrylate, 25% by weight butyl methacrylate and 50% by weight dimethylaminoethyl methacrylate, low molecular weight, renally eliminated Mw=21 000) are mixed and kept at 37° C. with slow stirring for about 30 minutes. The pH is measured after this time and adjusted to 7.4 with 0.001N HCl. Vigorous mixing, e.g. on a vortex, results in nanoparticles with an average diameter of about 250 nm on use of Lipofectin® and of about 150 nm on use of modified Eudragit® E. The suspension of the nanoparticles is purified by dialysis. The suspension can be further processed directly, or the nanoparticles can be separated by freeze drying.

Example 2

Nanoparticles Comprising Cationic and Anionic (Meth)Acrylate Copolymer

It is found in preliminary tests with suitable human cell cultures that an optimal transfection rate for the nucleic acid active ingredient can be achieved when a proportion of, for example, 10% of the anionic (meth)acrylate copolymer Eudragit® L (modified) is added to the cationic Eudragit® E (modified).

2 mg of DNA (nucleic acid active ingredient), e.g. a gene therapy vector composed of double-stranded plasmid DNA having, for example, 3000 to 10 000 base pairs, comprising a gene which is to be expressed in human cells and Intended to have a therapeutic effect, is dissolved in 4 ml of phosphate buffer of pH 7.4, and mixed with 2 ml of a mouse monoclonal anti-human DNA IgM solution (1 mg/ml) and incubated, at 37° C. for 1 hour. Then 1.1 ml, 4 ml (1 mg/ml) of modified Eudragit® E ((meth)acrylate copolymer of 25% by weight methyl methacrylate, 25% by weight butyl methacrylate and 50% by weight dimethylaminoethyl methacrylate, low molecular weight, renally eliminated Mw=about 21 000) and 0.4 ml (1 mg/ml) of modified Eudragit® L (copolymer of 50% by weight methyl methacrylate and 50% by weight methacrylic acid, low molecular weight, renally eliminated Mw=21 000) are mixed and kept at 37° C. with slow stirring for about 30 minutes. Vigorous mixing, e.g. on a vortex, results in nanoparticles with an average diameter of about 250 nm. The suspension of the nanoparticles is purified by dialysis. The suspension can be further processed directly, or the nanoparticles can be separated by freeze drying.

Example 3

Surface-Modified Nanoparticles (Nanoparticles Comprising Cationic (Meth)Acrylate Copolymer with a Shell of Anionic (Meth)Acrylate Copolymer)

2 mg of DNA (nucleic acid active ingredient), e.g. a gene therapy vector composed of double-stranded plasmid DNA having, for example, 3000 to 10 000 base pairs, comprising a gene which is to be expressed in human cells and intended to have a therapeutic effect, is dissolved in 4 ml of Dulbecco phosphate buffer of pH 7.4, and mixed with 2 ml of a mouse monoclonal anti-human DNA IgM solution (1 mg/ml) and incubated at 37° C. for 1 hour. Then 4 ml (1 mg/ml) of modified Eudragit® E ((meth)acrylate copolymer of 25% by weight methyl methacrylate, 25% by weight butyl methacrylate and 50% by weight dimethylaminoethyl methacrylate, low molecular weight, renally eliminated Mw=21 000) are mixed and kept at 37° C. with slow stirring for about minutes. The pH is measured after this time and adjusted to 7.4 with 0.001N HCl.

1 ml of a solution (1 mg/ml) of modified Eudragit® L ((meth)acrylate copolymer of 50% by weight methyl methacrylate and 50% by weight methacrylic acid, low molecular weight, renally eliminated, Mw=about 21 000) in phosphate buffer (pH 7.4, 0.5 mg/ml) is admixed, and the resulting latex-like buffer dispersion is with addition of a 0.001 M citric acid until pH 5.0 is reached. The suspension of the nanoparticles is purified by dialysis. The suspension can be further processed directly, or the enveloped nanoparticles can be separated by freeze drying.

Example 4

Production of Mucoadhesive as Yet Uncoated Pellets (Pre-Pellets) by Incorporating the Nanoparticles from Examples 1, 2 or 3 into an Inner Matrix Layer which Comprises Chitosan and is Adjusted to pH 5.0 to 5.5 with an Acid Preparation of a Mucoadhesive Solution:
4 g of chitosan acetate are dissolved in 20 g of water. Then, while stirring rapidly, 2 g of citric acid monohydrate are added. A pH of 5.2 is set. Then, 0.4 g of Na dodecanoate are added to the clear, yellowish viscous solution obtained. The suspensions from Example 1, 2 or 3 are mixed into this solution with slow stirring.
Production of Pre-Pellets
The mixed suspension is sprayed, using a fluidized bed apparatus (Micro-Lab from Hüttling) at a spray rate of 5-8 g/min/kg, onto 40 g of neutral pellets having a diameter of about 400-600 μm with an inlet air temperature of 30° C. The inlet air is in this case set at 35-45 m³/h. The yield in this case is 85-90%.

Example 5

Production of (Coated) Pellets

Pre-pellets produced as in Example 4 are coated in a fluidized bed process with Eudragit® L 12.5 ((meth)acrylate copolymer of 50% by weight methyl methacrylate and 50% by weight methacrylic acid, Mw=about 200 000, 12.5% strength organic solution in isopropanol/acetone 3:2). The application of polymer amounts to 40% by weight based on the core weight. The suspension for coating consists of:

| | |
|---|---|
| Eudragit ® L 12.5 | 53.5% |
| Triethyl citrate | 1.33% |
| Isopropanol | 38.3% |
| Talc | 2.0% |
| Water | 5.0% |

Uniformly enveloped pellets which are resistant to gastric juice and whose envelope rapidly dissolves above pH 6.0 in the duodenum or jejunum and releases the mucoadhesive pre-pellets are obtained.

Example 6

Production of a Multiparticulate Pharmaceutical Form in Capsule Form

Pellets produced as in Example 5 are packed by means of a capsule-filling apparatus into hard gelatin capsules, capsules of size 0, directly to give units with a filled weight of 550 mg. After oral administration, the capsule dissolves rapidly in the pH range of the stomach, and releases the pellets which are uniformly distributed even in the stomach.

Example 7

Production of a Multiparticulate Pharmaceutical Form in Tablet Form

Pellets produced as in Example 5 are formulated with tableting aids, binders, disintegration promoters and lubricants, 550 g of pellets are mixed with 390 g of microcrystalline cellulose, 150 g of Na carboxymethyl-starch and 10 g of Mg stearate. The mixture is compressed in a tablet press to compacts with a total weight of 1100 mg. After oral administration, the tablet disintegrates in the pH range of the stomach and releases the pellets, which are uniformly distributed even in the stomach.

The invention claimed is:

1. An oral multiparticulate pharmaceutical form comprising pellets having an average diameter in the range from 50 to 2500 μm, the pellets comprising
    a) an inner matrix layer comprising nanoparticles, wherein the nanoparticles comprise a nucleic acid active ingredient and are embedded into a matrix of a polymer having a mucoadhesive effect, wherein the matrix may optionally comprise pharmaceutically acceptable excipients, and
    b) an outer film coating comprising an anionic polymer or copolymer which may optionally be formulated with pharmaceutically acceptable excipients,
    wherein
    the multiparticulate pharmaceutical form is formulated so that the pellets are released in the pH range of the stomach, the outer film coating is adjusted through the choice of the anionic polymer or copolymer and its formulation with the excipients and its layer thickness so that the outer film coating dissolves in a pH range from 4.0 to 8.0 in the intestine within 15 to 60 min so that the inner matrix layer is exposed and can bind to the intestinal mucosa and release the nucleic acid active ingredient into the intestinal mucosa, wherein the polymer having a mucoadhesive effect exhibits a mucoadhesive effect of at least $\eta_b$=150 to 1000 mPa·s and a water uptake of from 10 to 750% in 15 min in a range of +/−0.5 pH units relative to the pH at which the outer film coating starts to dissolve, and the nucleic acid active ingredient of the nanoparticles in the inner matrix layer is a maximum of 40% by weight of the content of the polymers having a mucoadhesive effect
    wherein the nucleic acid active ingredient in the nanoparticles is present in the form of a complex with a cationic substance that is a cationic lipid, a cationic polypeptide or a cationic polymer and an anionic (meth)acrylate copolymer.

2. The pharmaceutical form according to claim 1, wherein the nanoparticles have a size in the range from 20 to 1000 nm.

3. The pharmaceutical form according to claim 1, wherein the cationic substance is a cationic lipid, a cationic polypeptide and/or a cationic polymer.

4. The pharmaceutical form according to claim 3, wherein the cationic polymer is a (meth)acrylate copolymer which has tertiary or quaternary amino groups.

5. The pharmaceutical form according to claim 4, wherein the (meth)acrylate copolymer comprising free-radical polymerized units of 20 30% by weight methyl methacrylate, 20 30% by weight butyl methacrylate and 60 40% by weight dimethylaminoethyl methacrylate.

6. The pharmaceutical form according to claim 1, wherein the anionic (meth)acrylate copolymer comprises monomers having anionic groups of from 5 to 60% by weight.

7. The pharmaceutical form according to claim 1, wherein the anionic (meth)acrylate copolymer comprises
    20 to 33% by weight methacrylic acid and/or acrylic acid,
    5 to 30% by weight methyl acrylate and
    20 to 40% by weight ethyl acrylate and
    more than 10 to 30% by weight butyl methacrylate and, if present,
    0 to 10% by weight further monomers capable of vinylic copolymerization, wherein the proportions of the monomers add up to 100% by weight, with the proviso that the glass transition temperature of the copolymer according to ISO 11357 2, subsection 3.3.3 (midpoint temperature $T_{mg}$) is from 55 to 70° C.

8. The pharmaceutical form according to claim 1, wherein the anionic (meth)acrylate copolymer has an average molecular weight $M_w$ of 50 000 or less.

9. The pharmaceutical form according to claim 1, wherein the nanoparticles have an encapsulation with an anionic (meth)acrylate copolymer having an average molecular weight $M_w$, of 50 000 or less.

10. The pharmaceutical form according to claim 1, wherein the nucleic acid active ingredient is selected from the group consisting of a single-stranded DNA, double-stranded DNA, RNA, and a DNA-RNA chimera, wherein naturally occurring nucleotides, and/or non-naturally occurring synthetically modified nucleotides or a combination thereof optionally occur.

11. The pharmaceutical form according to claim 1, wherein the nucleic acid active ingredient comprises a complex of an antibody, which binds specifically to a nucleic acid of the nucleic acid active ingredient, and a cationic substance.

12. The pharmaceutical form according to claim 1, wherein the outer film coating is cellulose glycolate, cellulose acetate phthalate, cellulose acetate succinate (CAS), cellulose acetate trimeliate (CAT), hydroxypropyl-methylcellulose phthalate (HPMCP, HP50, HP55), hydroxypropylmethylcellulose acetate succinate (HPMCAS-LF, -MF, -HF), polyvinyl acetate phthalate, vinyl acetate-vinylpyrrolidone copolymer, vinyl acetate:crotonic acid 9:1 copolymer and/or shellac.

13. The pharmaceutical form according to claim 1, wherein the outer film coating is a (meth)acrylate copolymer having a content of monomers having anionic groups of from 5 to 60% by weight.

14. The pharmaceutical form according to claim 1, wherein the layer thickness of the outer film coating is in the range from 20 to 200 um.

15. The pharmaceutical form according to claim 1, wherein the inner matrix layer comprises a $C_{10}$ to $C_{20}$ fatty acid and/or a $C_{10}$ to $C_{20}$ alcohol including their salts, ether, ester or amide derivatives, and/or a lipid, and/or a phospholipids, and/or a lipid-soluble vitamin, and/or a penetration promoter.

16. The pharmaceutical form according to claim 1, wherein the polymer having a mucoadhesive effect is a chitosan, a (meth)acrylate copolymer consisting of 20 40% by weight methyl methacrylate and 60 to 80% by weight methacrylic acid and/or a cellulose, Na carboxymethylcellulose, a crosslinked and/or uncrosslinked polyacrylic acid, a lectin, an Na alginate, and/or a pectin.

17. The pharmaceutical form according to claim 16, wherein the inner matrix layer comprises the polymer having a mucoadhesive effect which is a chitosan, which is employed together with an acid or a buffer system which is present in the matrix or in or on a core onto which the matrix is applied.

18. The pharmaceutical form according to claim 17, wherein the inner matrix layer comprises chitosan and is adjusted to pH 5.0 to 5.5 with an acid or a buffer system, and is combined with an outer film coating which starts to dissolve in the region of pH 6.0 to 8.0.

19. The pharmaceutical form according to claim 1, wherein a separating layer is applied between the inner matrix layer comprising the nucleic acid active ingredient and the outer film coating layer.

20. A process for producing a multiparticulate pharmaceutical form of claim 1, comprising:

a) complexing the nucleic acid active ingredient with the cationic substance and the anionic (meth)acrylate copolymer, optionally in the presence of pharmaceutically acceptable excipients, b) formulating an inner matrix layer comprising the nucleic acid active ingredient in the form of nanoparticles and a polymer having a mucoadhesive effect and, optionally, pharmaceutically acceptable excipients by means of spray application onto a core or by rotagglomeration, precipitation or spray processes without a core to form pre-pellets, c) applying an outer film coating consisting essentially of an anionic polymer, which may optionally be formulated with pharmaceutically acceptable excipients, by spray application to the pre-pellets to obtain resulting active ingredient-containing enveloped pellets, and d) processing the resulting pellets to formulate the multiparticulate pharmaceutical form, wherein the resulting pellets are released in the pH range of the stomach.

21. The multiparticulate pharmaceutical form according to claim 1, wherein the pharmaceutically acceptable excipients are plasticizers.

22. The process for producing a multiparticulate pharmaceutical form according to claim 20, wherein the pharmaceutically acceptable excipients are plasticizers.

23. The pharmaceutical form according to claim 1, wherein the pellets have a average diameter of 100 to 2500 μm.

24. The pharmaceutical form according to claim 1, wherein the outer film coating dissolves in a pH range from 5.5 to 7.8.

25. The pharmaceutical form according to claim 1, wherein the polymer having a mucoadhesive effect exhibits a water uptake of from 10 to 250% in 15 minutes in a range of +/−0.5 pH unites relative to the pH at which the outer film coating starts to dissolve.

26. The pharmaceutical form according to claim 3, wherein the cationic substance is a cationic copolymer that has an average molecular weight $M_w$ of 50 000 or less.

* * * * *